US008685699B2

(12) United States Patent
Leu et al.

(10) Patent No.: US 8,685,699 B2
(45) Date of Patent: Apr. 1, 2014

(54) **METHOD FOR PRODUCING OIL BY *CYSTOFILOBASIDIUM* SPP**

(75) Inventors: Jyh-Yih Leu, Taipei (TW); Yu-Di Hsu, Tainan County (TW); Yu-Sheng Wu, Taipei County (TW)

(73) Assignee: Fu-Jen Catholic University, Taipei (TW)

( * ) Notice: Subject to any disclaimer, the term of this patent is extended or adjusted under 35 U.S.C. 154(b) by 62 days.

(21) Appl. No.: 13/204,116

(22) Filed: Aug. 5, 2011

(65) Prior Publication Data

US 2012/0040419 A1 Feb. 16, 2012

(30) Foreign Application Priority Data

Aug. 13, 2010 (TW) .............................. 99127213 A

(51) Int. Cl.
*C12N 1/12* (2006.01)
*C12P 7/64* (2006.01)

(52) U.S. Cl.
USPC ...................................... 435/252.1; 435/134

(58) Field of Classification Search
None
See application file for complete search history.

(56) References Cited

U.S. PATENT DOCUMENTS

| 7,659,409 B2 | 2/2010 | Takehara et al. |
| 2008/0171379 A1* | 7/2008 | Donndelinger .............. 435/264 |

FOREIGN PATENT DOCUMENTS

| WO | 2009/046231 | 4/2009 |
| WO | 2009/126843 | 10/2009 |

OTHER PUBLICATIONS

Libkind et al. Fatty acid composition of cold-adapted carotenogenic basidiomycetous yeasts, Revista Argentina de Microbiologia (2008) 40: 193-197.*
Fell et al., "The Potential Use of Sterols and Phospholid Fatty Acids as Taxonomic Tools among Teliospore—forming Red Yeasts," International Symposium on the Perspectives of Taxonomy 30, pp. 309-320 (1987).
Libkind et al., "Fatty Acid Composition of Cold-Adapted Carotenogenic Basidiomycetous Yeasts," Revista Argentina de Microbiologa 40, pp. 193-197 (2008).
Van Der Westhuizen et al., "The Potential Use of Cellular Long-chain Fatty Acid Composition in the Taxonomy of the Carotenoid Pigment Producing Genera Rhodosporidium Banno and Rhodotorula Harrison," System. Appl. Microbiol. 14, pp. 282-290 (1991).

* cited by examiner

*Primary Examiner* — Iqbal H Chowdhury
(74) *Attorney, Agent, or Firm* — Volpe and Koenig, P.C.

(57) ABSTRACT

An oil generation system is provided. The oil generation system includes a saccharide; and a working microorganism reacting with the saccharide to produce an oil, wherein the working microorganism has a genus being a *Cystofilobasidium*.

17 Claims, 13 Drawing Sheets

(1 of 13 Drawing Sheet(s) Filed in Color)

```
                        SEQUENCE LISTING

<160> NUMBER OF SEQ ID NOS: 9

<210> SEQ ID NO 1
<211> LENGTH: 24
<212> TYPE: DNA
<213> ORGANISM: Cystofilobasidium sp.
<220> FEATURE:
<223> OTHER INFORMATION: 18S rDNA forward primer sequence

<400> SEQUENCE: 1
gcatatcaat aagcggagga aaag                                            24

<210> SEQ ID NO 2
<211> LENGTH: 18
<212> TYPE: DNA
<213> ORGANISM: Cystofilobasidium sp.
<220> FEATURE:
<223> OTHER INFORMATION: 18S rDNA reverse primer sequence

<400> SEQUENCE: 2
ggtccgtgtt tcaagacg                                                   18

<210> SEQ ID NO 3
<211> LENGTH: 19
<212> TYPE: DNA
<213> ORGANISM: Cystofilobasidium sp.
<220> FEATURE:
<223> OTHER INFORMATION: ITS forward primer sequence,ITS1

<400> SEQUENCE: 3
tccgtaggtg aacctgcgg                                                  19
```

```
<210> SEQ ID NO 4
<211> LENGTH: 20
<212> TYPE: DNA
<213> ORGANISM: Cystofilobasidium sp.
<220> FEATURE:
<223> OTHER INFORMATION: ITS reverse primer sequence,ITS4

<400> SEQUENCE: 4
tcctccgctt attgatatgc                                              20

<210> SEQ ID NO 5
<211> LENGTH: 24
<212> TYPE: DNA
<213> ORGANISM: Cystofilobasidium sp.
<220> FEATURE:
<223> OTHER INFORMATION: 26S D1/D2 forward primer sequence, F63

<400> SEQUENCE: 5
gcatatcaat aagcggagga aaag                                         24

<210> SEQ ID NO 6
<211> LENGTH: 19
<212> TYPE: DNA
<213> ORGANISM: Cystofilobasidium sp.
<220> FEATURE:
<223> OTHER INFORMATION: 26S D1/D2 reverse primer sequence, LR3

<400> SEQUENCE: 6
ggtccgtgtt tcaagacgg                                               19

<210> SEQ ID NO 7
<211> LENGTH: 1196
<212> TYPE: DNA
<213> ORGANISM: Cystofilobasidium sp.
<220> FEATURE:
<223> OTHER INFORMATION: 18S rDNA sequence of TN01

<400> SEQUENCE: 7
gatttaaacg ttccctagta cggcgagtga gcgggaagag ctcaaattta aaatctggca    60
gtctacgatt gtccgaattg taatctcgag aagtgttttc gcgttggcc tgtgtacaag    120 tcccttggaa cagggcgtca tagagggtga gaatcccgtc cttgacacag acacccaatg   180
ctttgtgata cactctcaat gagtcgagtt gtttgggaat gcagctcaaa atgggtggta   240
aattccatct aaagctaaat actggcgaga gaccgatagc gaacaagtac cgtgagggaa   300
agatgaaaag cactttggaa agagagtcaa acagtacgtg aaattgttga agggaaacg    360 attgaagtca gtcgtgcctg cctagattca gccttctggt gtatttctag gtcggcaggt   420
cagcatcagt ttggggggt taacaaggga gttaggaatg tagcaacctc ggttgtgtta    480
tagcctagct tcgcattgat ctcgctggac tgaggaacgc agtgcgcccg caagggttgg   540
tcttcggaca cattcgcact taggatgctg gcataatggc tttaaacgac ccgtcttgaa   600
aacggaggaa aagaaactaa caaggattcc cctagtaacg gcgagtgaag cgggaagagc   660
tcaaatttaa aatctggcag tctacgattg tccgaattgt aatctcgaga agtgttttcc   720
gcgttggcct gtgtacaagt cccttggaac agggcgtcat agagggtgag aatcccgtcc   780
ttgacacaga cacccaatgc tttgtgatac actctcaatg agtcgagttg tttgggaatg   840
cagctcaaaa tgggtggtaa attccatcta aagctaaata ctggcgagag accgatagcg   900
aacaagtacc gtgagggaaa gatgaaaagc actttggaaa gagagtcaaa cagtacgtga   960
aattgttgaa agggaaacga ttgaagtcag tcgtgcctgc ctagattcag ccttctggtg  1020
tatttctagg tcggcaggtc agcatcagtt tggggggtt aacaagggag ttaggaatgt   1080
```

```
agcaacctcg gttgtgttat agcctagctt cgcattgatc tcgctggact gaggaacgca    1140
gtgcgcccgc aagggttggt cttcggacac attcgcacta ggatgctgca tagtcc        1196

<210> SEQ ID NO 8
<211> LENGTH: 1230
<212> TYPE: DNA
<213> ORGANISM: Cystofilobasidium sp.
<220> FEATURE:
<223> OTHER INFORMATION: 26S rDNA D1/D2 sequence of TN01

<400> SEQUENCE: 8
acccctagta acggcgagtg aagcgggaag agctcaaatt taaaatctgg cagtctacga      60
ttgtccgaat tgtaatctcg agaagtgttt tccgcgttgg cctgtgtaca agtcccttgg    120
aacagggcgt catagagggt gagaatcccg tccttgacac agacacccaa tgctttgtga    180
tacactctca atgagtcgag ttgtttggga atgcagctca aaatgggtgg taaattccat    240
ctaaagctaa atactggcga gagaccgata gcgaacaagt accgtgaggg aaagatgaaa    300
agcactttgg aaagagagtc aaacagtacg tgaaattgtt gaaagggaaa cgattgaagt    360
cagtcgtgcc tgcctagatt cagccttctg gtgtatttct aggtcggcag gtcagcatca    420
gtttgggggg gttaacaagg gagttaggaa tgtagcaacc tcggttgtgt tatagcctag    480
cttcgcattg atctcgctgg actgaggaac gcagtgcgcc cgcaagggtt ggtcttcgga    540
cacattcgca cttaggatgc tggcataatg gctttaaacg accgtcttg aaccaacggg     600 accaatttat tatgcatatc caaaagcgg aggaaaagaa actaacaagg attcccctag      660
taacggcgag tgaagcggga agagctcaaa tttaaaatct ggcagtctac gattgtccga    720
attgtaatct cgagaagtgt tttccgcgtt ggcctgtgta caagtccctt ggaacagggc    780
gtcatagagg gtgagaatcc cgtccttgac acagacaccc aatgctttgt gatacactct    840
caatgagtcg agttgtttgg gaatgcagct caaaatgggt ggtaaattcc atctaaagct    900
aaatactggc gagagaccga tagcgaacaa gtaccgtgag ggaaagatga aaagcacttt    960
ggaaagagag tcaaacagta cgtgaaattg ttgaaaggga aacgattgaa gtcagtcgtg   1020
cctgcctaga ttcagccttc tggtgtattt ctaggtcggc aggtcagcat cagtttgggg   1080
gggttaacaa gggagttagg aatgtagcaa cctcggttgt gttatagcct agcttcgcat   1140
tgatctcgct ggactgagga acgcagtgcg cccgcaaggg ttggtcttcg gacacattcg   1200
cacttaggat gctgccaaag tcaagaaggt                                     1230

<210> SEQ ID NO 9
<211> LENGTH: 1212
<212> TYPE: DNA
<213> ORGANISM: Cystofilobasidium sp.
<220> FEATURE:
<223> OTHER INFORMATION: ITS sequence of TN01

<400> SEQUENCE: 9
gcaaagggat cgccttcggg gctctctacc ctttcacacc cctgtgcact ttggccgccg     60
cttcattgcg gttggtcttt ttttaccata cccatataca caagtcattg aatgtaaaat    120
cgttataaac taatataact ttcaacaacg gatctcttgg ttctcgcatc gatgaagaac    180
gcagcgaatt gcgataagta atgtgaattg cagaattcag tgaatcatcg aatctttgaa    240
cgcatcttgc gctctttggt attccgaaga gcatgcctgt ttgagtgtca tgaaactctc    300
acctccagcc gttttttaat tagagcgtgt tgggcgtgg atgtgagtgc tgctggtgcc     360
ctggttgcat cggctcactt gaaatttatt agctgaatcc tctagagttg gttctactcg    420
```

```
                                                          -continued
acgtgataag tatctccgtc gaggacagtt ggtcttgtcc ttatgggcgg ggtccgctgg    480
ccaacgatag cagttgatac gcttctaatt agcgcagact tcgagtgctg gcaactttga    540
caacttggcc tcaaatcagg taggactacc cactgaactt aagcatatca ataagcggag    600
gaagatctct tccgtagggg aacctgcgga aggatcacta gagaatatcg cccttcgggg    660
ctctctaccc tttcacaccc ctgtgcactt tggccgccgc ttcattgcgg ttggtctttt    720
tttaccatac ccatatacac aagtcattga atgtaaaatc gttataaact aatataactt    780
tcaacaacgg atctcttggt tctcgcatcg atgaagaacg cagcgaattg cgataagtaa    840
tgtgaattgc agaattcagt gaatcatcga atctttgaac gcatcttgcg ctctttggta    900
ttccgaagag catgcctgtt tgagtgtcat gaaactctca cctccagccg tttttaatt     960 agagcgtgtt ggggcgtgga tgtgagtgct gctggtgccc tggttgcatc ggctcacttg   1020
aaatttatta gctgaatcct ctagagttgg ttctactcga cgtgataagt atctccgtcg   1080
aggacagttg gtcttgtcct tatgggcggg gtccgctggc caacgatagc agttgatacg   1140
cttctaatta gcgcagactt cgagtgctgg caactttgac aactggcctc aaatcaggta   1200
gacagcccca ac                                                       1212
```

METHOD FOR PRODUCING OIL BY *CYSTOFILOBASIDIUM* SPP

CROSS-REFERENCE TO RELATED APPLICATION AND CLAIM OF PRIORITY

The application claims the benefit of Taiwan Patent Application No. 099127213, filed on Aug. 13, 2010, in the Taiwan Intellectual Property Office, the disclosures of which are incorporated herein in their entirety by reference.

FIELD OF THE INVENTION

The present invention relates to an oil generation system, and more particularly to an oil generation system by using *Cystofilobasidium* spp.

BACKGROUND OF THE INVENTION

Currently, the bioenergy is approximately divided into two categories, wherein one is alcohol, and the other is biodiesel oil. The manufacture of bioalcohol utilizes the grain as materials. Recently, the researches gradually turn to generating bioalcohol by microorganisms. There have been many researches pointing out that microorganisms have high potential for generating alcohol. As to the biodiesel oil, it is manufactured from plant materials, discarded edible oil or animal fat. The plant materials mainly are oil grains, such as the soybean, the maize, the rapeseed, the palm, the seed of *Jatropha curcushas*, the sunflower, etc.; discarded edible oil and animal fat are purified and extracted again to generate biodiesel oil. Both resources of biodiesel oils cannot satisfy the requirements of actual use, and have drawbacks respectively. The oil crop needs a large range of growing land, the crop has seasonal factors, the bioenergy provided by an unit land does not conform to the economic efficiency, there is a problem of competing food with the people, and the extracting procedure is very complex and the cost thereof is high, so the oil crop cannot become the material continuously providing biodiesel oil to replace the petroleum. Discarded edible oil and animal fat have the problems of low quantity, breeding and environmental pollution. Thus, recently the trend is to produce biodiesel oil by the microorganisms. According to researches, the microorganisms can provide 40% of the replaced energy required by the transportation only through occupying 1-3% of the crop growing land, and have rather high potential and advantages.

Utilizing microorganisms to produce oil is not a recent idea. Besides the microalgae and the bacteria, there are oil-generating microorganisms in fungi, most of which are yeast and mould, and some microorganisms simultaneously have the characteristic of generating long-chain saturated fatty acid, monounsaturated fatty acid or polyunsaturated fatty acid. These oil-generating yeasts can produce fatty acid occupied over 40% of biomass and accumulated up to 70% via the limitation and allocation of the medium, which have rather high potential for producing oil. Table 1 shows common oil-generating fungi and the oil quantity produced thereby (Beopoulos, et al., 2009; Gill, Hall, & Ratledge, 1977; Ratledge, 1993, 2002, 2004; Sergeeva Ia, Galanina, Andrianova, & Feofilova, 2008; Zhao, et al., 2010).

TABLE 1

| Fungi | Lipid % of dry weight (w/w) |
|---|---|
| *Aspergillus terreus* | 64 |
| *Cryptococcus curvatus* | 58 |
| *Cryptococcus albidus* | 65 |
| *Candida* sp. | 42 |
| *Cunninghamella japonica* | >43.8 |
| *Lipomyces starkeyi* | 63 |
| *Penicillium spmulosum* | 64 |
| *Rhodosporidium toruloides* | 56.5 |
| *Rhodotorula glutinis* | 72 |
| *Rhodotorula graminis* | 36 |
| *Rhizopus arrhizus* | 57 |
| *Schizochytrium* spp. | 30~50 |
| *Thraustochytrium* spp. | 30~50 |
| *Trichosporon pullulans* | 65 |
| *Yarrowia lipolytica* | 36 |

SUMMARY OF THE INVENTION

In accordance with one aspect of the present invention, an oil generation system is provided. The system includes a saccharide and a working microorganism reacting with the saccharide to produce an oil, wherein the working microorganism has a genus being a *Cystofilobasidium*.

In accordance with another aspect of the present invention, an oil generation system is provided. The system includes a carbon source and a working microorganism reacting with the carbon source to produce an oil, wherein the working microorganism has a genus being a *Cystofilobasidium*.

In accordance with a further aspect of the present invention, a method for producing an oil is provided. The method includes a step of utilizing an oil-generating microorganism to produce the oil, wherein the oil-generating microorganism has a genus being a *Cystofilobasidium*.

The above objects and advantages of the present invention will become more readily apparent to those ordinarily skilled in the art after reviewing the following detailed descriptions and accompanying drawings, in which:

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

Shape Observation

Figures 1A, 1B, 1C, 1D:
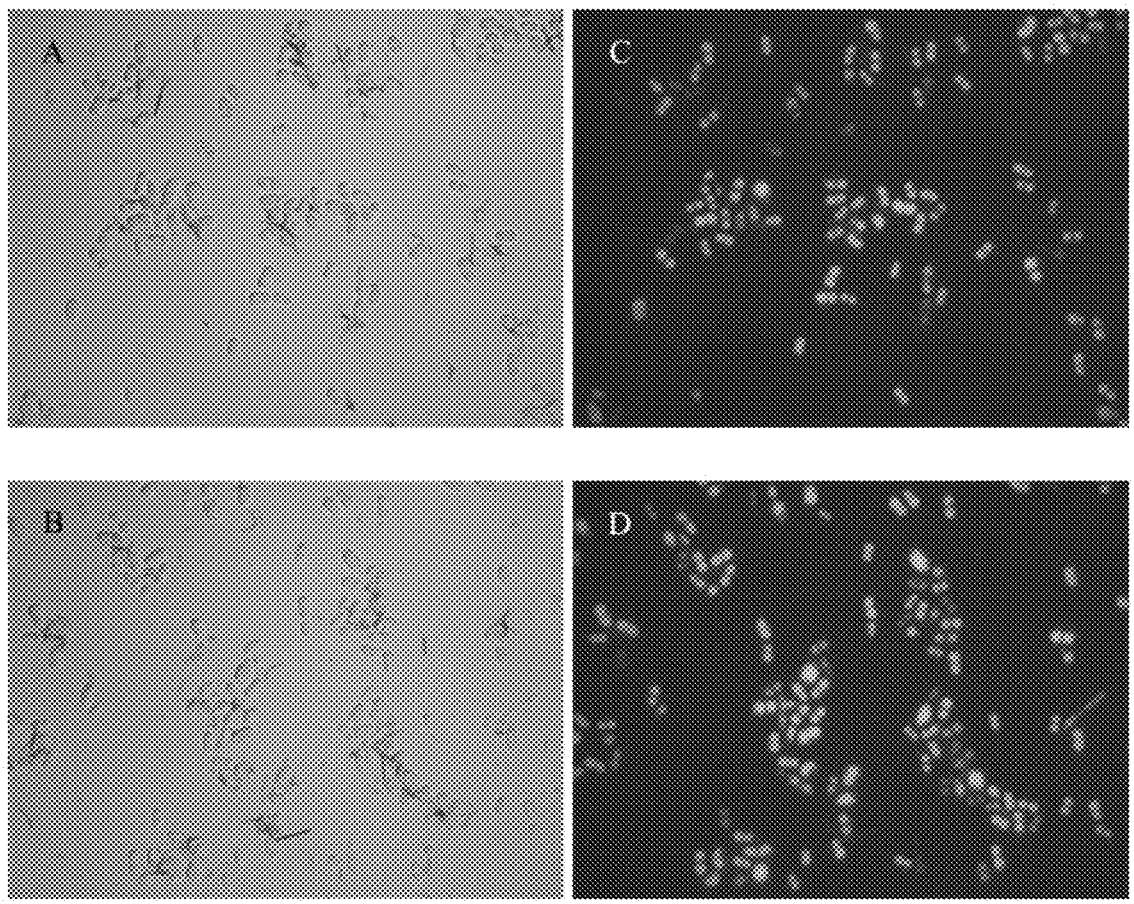
FIGS. 1A-1D show the shape of TN01 strain and the oil dyeing result thereof by the optical microscope and fluorescence microscope (1000×)

The experimental strain is sampled from the coastal area of Tainan, Taiwan. The anti-LgYPG medium is used for the first sieving. Colonies with different appearances are picked out to be observed by the optical microscope, and the observation results are shown in FIGS. 1A-1B, wherein the appearance of the colony is circle, the surface thereof appears smooth and neat, like the shine of wax, and the color thereof is pink. The sample after the first sieving is cultured in LgYPG medium at 20° C. for 7 days, which is the second sieving. The colonies after the second sieving are dyed with Nile red, and observed by the fluorescence microscope. The observation results are shown in FIGS. 1C-1D, and the parts with oil will appear golden color. After the observation, the strain with oil is cultured in GYPG medium at 20° C. for 7 days, and the purification is repeated for 3 times to obtain the experimental strain.

A. Anti-LgYPG Solid Medium

| | |
|---|---|
| Glucose | 2% |
| Peptone | 0.1% |
| Yeast extract | 0.1% |
| Gelatin | 0.1% |
| Agar | 1.2% |
| Diluted seawater | 50% |
| Streptomycin | 0.1 g/L |

B. The prescription of LgYPG medium is the same as Anti-LgYPG, but without streptomycin.

C. The prescription of GYPG solid medium is the same as LgYPG, but the concentration of glucose is adjusted to 5%.

D. The prescription of GYPG liquid medium is the same as GYPG, but without agar.

After many times of purification and isolation, the microorganisms with oil are sieved out and numbered TN01-TN09, which are confirmed as purified strains. Since the sieved TN series are very similar, in the following experiments, TN01 is selected randomly as the research object of the optimal cultured condition.

Figures 2A, 2B:
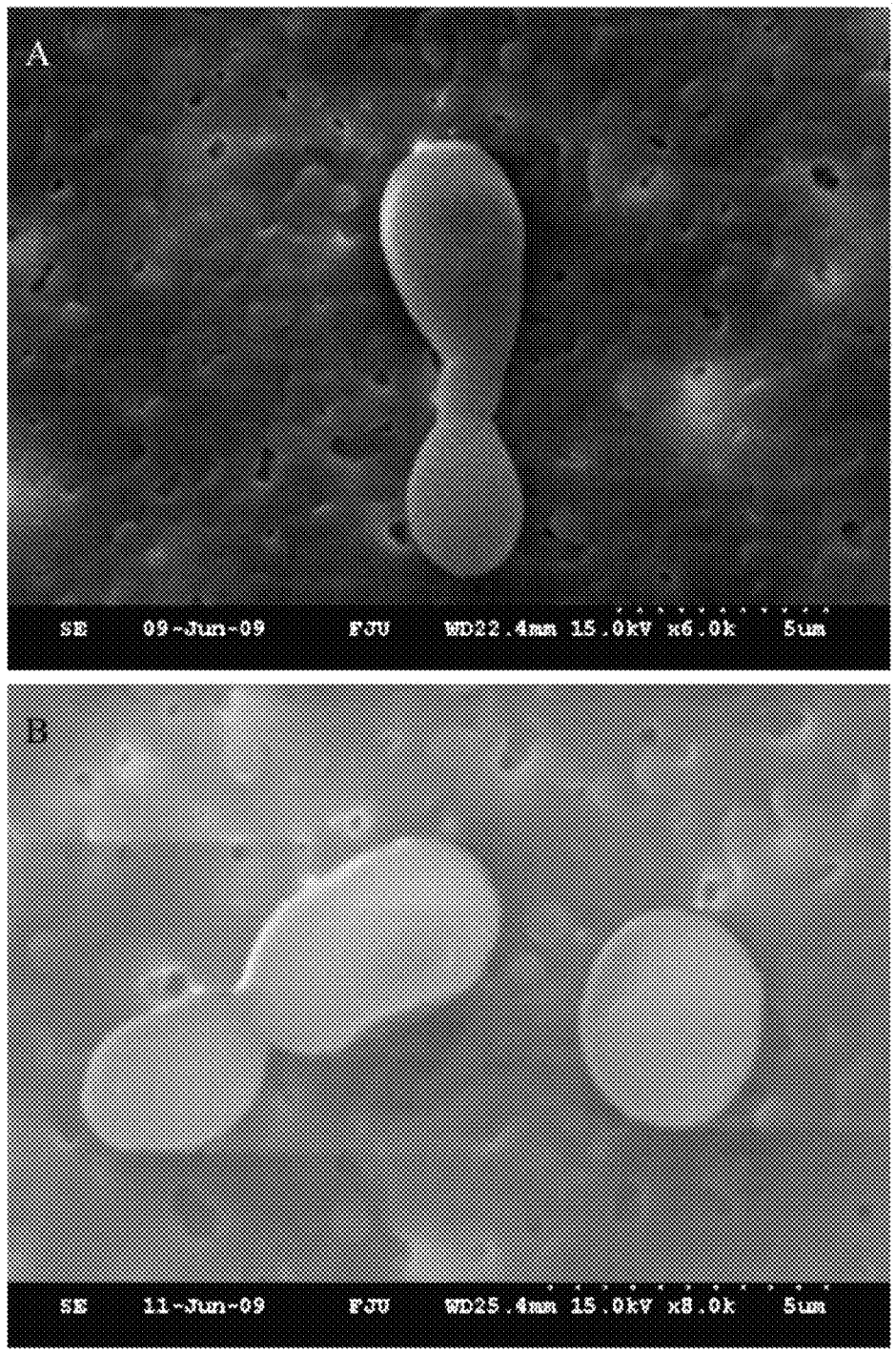
FIGS. 2A-2B show the shape of TN01 strain by the scanning electron microscope.

TN01 is further observed with the scanning electron microscope. The results are shown in FIGS. 2A-2B. TN01 is an oval-shaped body, which is smooth without any wrinkles or protuberances. TN01 has no mycelium and has the form similar to protogenesis, and hence it is conjectured as *Saccharomyces* according to the shape.

Sequence Identification and Phylogenetic Tree of Strain DNA Extraction

A. Take 1 ml cultural medium containing TN01 and proceed centrifugal separation to collect the fungus bodies, and then wash them with 1M NaCl for 3 times.

B. Add 200 μl lysis buffer and 20 μl protease K, at 55° C. overnight.

C. Add CTAB extraction solution up to total 1 ml and react at 65° C. for 30 min.

D. Add 400 μl chloroform and mix well for 30 sec.

E. Centrifugate at 14000 rpm and take the suspension.

F. Add 2 volumes of CTAB precipitating solution and place for 60 min

G. After centrifugation at 14000 rpm, collect precipitation and re-dissolve precipitation with 350 μl 1.2M NaCl.

H. Add 350 μl chloroform, mix well for 30 sec and centrifugate to take the suspension.

I. Add 0.8 volume of isopropanol and place at −20° C. for 30 min to precipitate DNA.

J. Centrifugate at 14000 rpm, remove the suspension, add 500 μl 70% alcohol to wash the DNA precipitation, centrifugate, and then dry DNA under room temperature.

K. Add 20 μl pH8, sterilized ddH$_2$O to re-dissolve at 37° C.

L. Proceed gel electrophoresis to confirm the size of DNA. The used marker is Bio-1 KB DNA Ladder (Protech).

Lysis Buffer

| Prescription | Concentration |
|---|---|
| SDS | 2% |
| Tris-HCl | 0.25M |
| Na$_2$•EDTA | 0.1M |
| NaCl | 0.1M |

Dissolve the prescription with dH$_2$O, adjust the pH value with HCl or NaOH to 8.2, and sterilize by autoclave.

CTAB Extraction Solution

| Prescription | Concentration (g/L) |
|---|---|
| NaCl | 81.8 |
| Tris | 12.1 |
| Na$_2$•EDTA | 7.4 |
| CTAB | 20 |

Dissolve the prescription with dH$_2$O, adjust the pH value with HCl or NaOH to 8.0, and sterilize by autoclave.

CTAB Precipitating Solution

| Prescription | Concentration (g/L) |
|---|---|
| NaCl | 2.3 |
| CTAB | 5 |

Dissolve the prescription with dH$_2$O and sterilize by autoclave.

Polymerase Chain Reaction (PCR)

This experiment is the sequence amplification for strain identification, and 3 pairs of primers are used. The sequences and the conditions are as follows.

| Primers of 18S sequencing | | |
|---|---|---|
| Name | Sequence (Fell, Roeijmans, & Boekhout, 1999) | |
| 18SF (Forward) | 5'-GCATATCAATAAGCGGAGGAAAAG-3' | SEQ ID NO.1 |
| 18SR (Reverse) | 5'-GGTCCGTGTTTCAAGACG-3' | SEQ ID NO.2 |
| Primers of ITS sequencing | | |
| Name | Sequence (Gadanho & Sampaio, 2002) | |
| ITS1 (Forward) | 5'-TCCGTAGGTGAACCTGCGG-3' | SEQ ID NO.3 |
| ITS4 (Reverse) | 5'-TCCTCCGCTTATTGATATGC-3' | SEQ ID NO.4 |
| Primers of 26S D1/D2 sequencing | | |
| Name | Sequence (Fell, et al., 2000) | |
| F63 (Forward) | 5'-GCATATCAATAAGCG GAGGAAAAG-3' | SEQ ID NO.5 |
| LR3 (Reverse) | 5'-GGTCCGTGTTTCAAGACGG-3' | SEQ ID NO.6 |

Reactants of PCR

| Reactant | Volume | Final Concentration |
|---|---|---|
| DNA | 4 μl | — |
| dNTP | 8 μl | 2.5 mM |
| 10X buffer | 5 μl | — |
| Primer (Forward) | 1 μl | — |
| Primer (Reverse) | 1 μl | — |
| Taq | 0.1 μl | 1 U |
| ddH$_2$O | 30.9 μl | — |
| Total | 50 μl | — |

Amplified Condition of PCR

| | Temperature | Time |
|---|---|---|
| | 94° C. | 5 min |
| | 94° C. | 1 min |
| 35 cycle | 57° C. | 1 min |
| | 72° C. | 2 min |
| | 72° C. | 10 min | i. After amplification for each condition, proceed 1% gel electrophoresis to confirm the size of DNA.

ii. The used marker is Bio-1 KB DNA Ladder (Protech).

Analysis of Comparing Sequences

After PCR amplification of 18S rDNA, 26S rDNA D1/D2 and ITS, all sizes of which are around 1200 base pairs. After BLAST comparing, the sequence of TN01 is the most similar to *Cystofilobasidium*.

Figure 3:
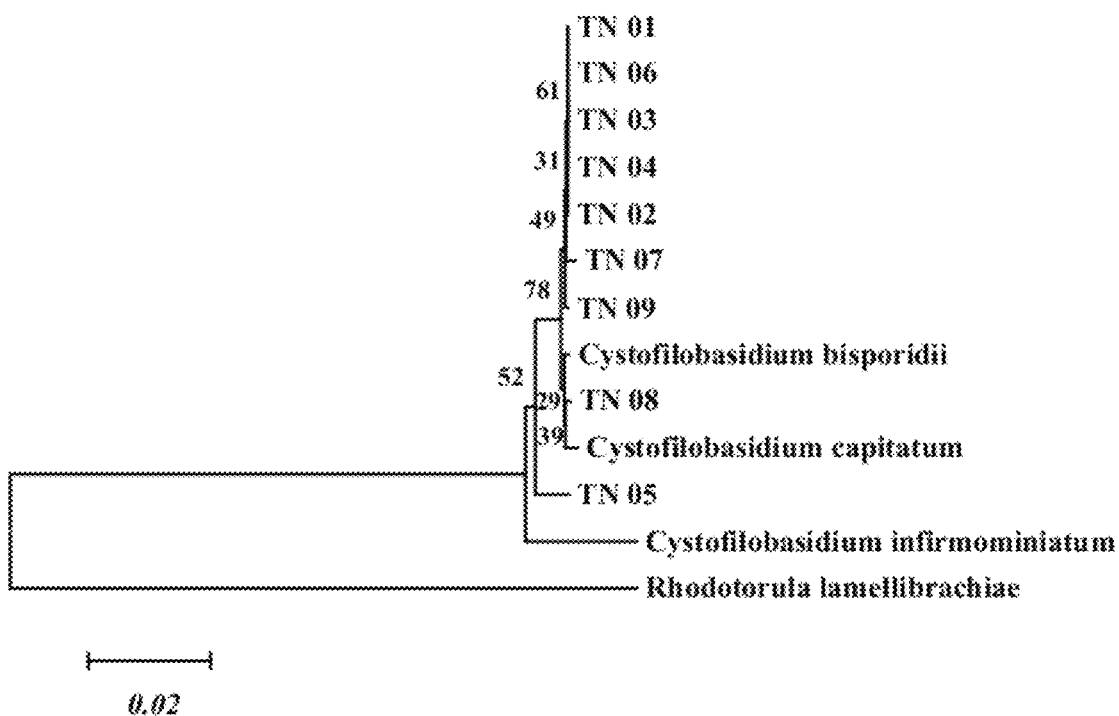
FIG. 3 shows the phylogenetic tree of 18S rDNA sequence identification.
Figure 4:
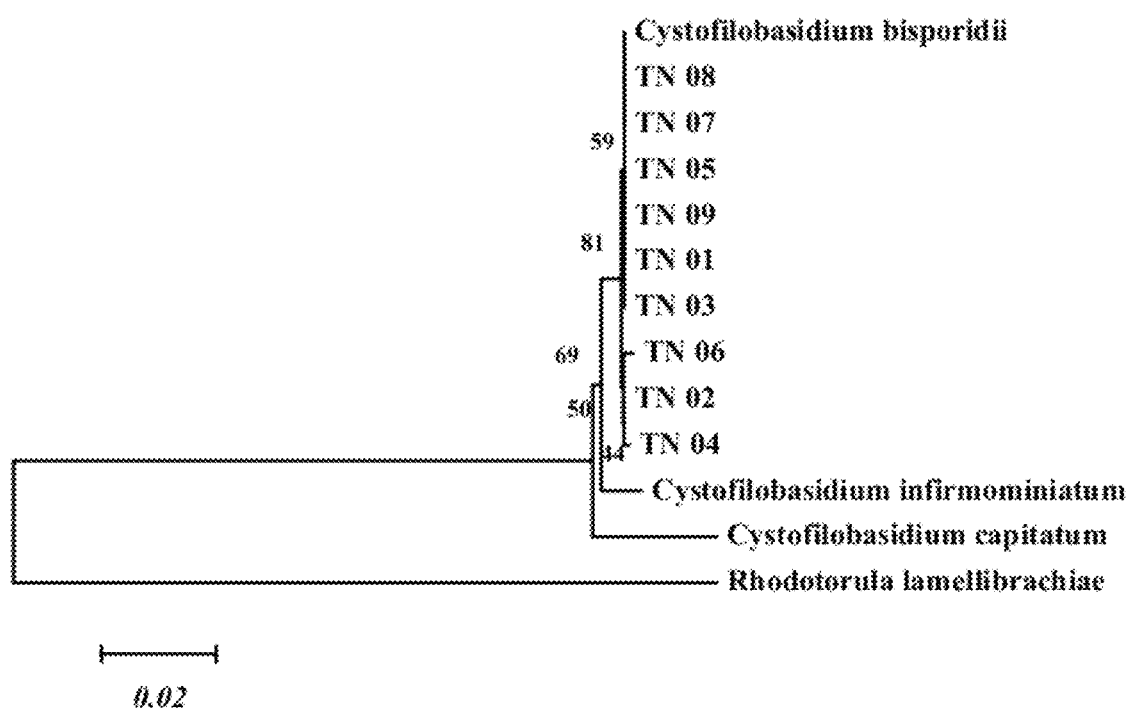
FIG. 4 shows the phylogenetic tree of 26S rDNA sequence identification.
Figure 5:
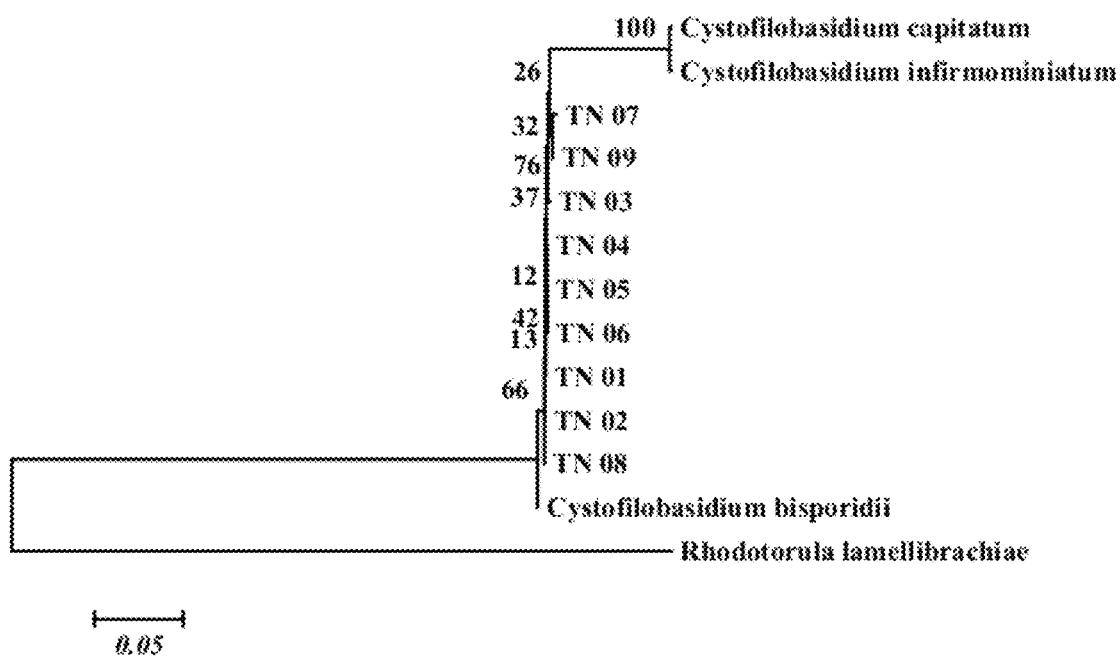
FIG. 5 shows the phylogenetic tree of ITS sequence identification.

Each sequence is arranged by Clustal W tool module, and analyzed by biology analysis software MEGA 4. Besides, classified methods of bootstrap test and neighbor-joining are used to establish the phylogenetic tree between TN series and standard strain. FIG. 3 shows the phylogenetic tree of 18S rDNA sequence; FIG. 4 shows the phylogenetic tree of 26S rDNA D1/D2 sequence; and FIG. 5 shows the phylogenetic tree of ITS sequence. *Rhodotorula lamellibrachiae* is another oil-generating fungus and serves as a control. It can be seen from FIGS. 3-5 that TN series are the most similar to the standard strain *Cystofilobasidium*, but still have some differences therebetween.

Biochemical Quality Test

The biochemical quality test of carbon source is performed for the isolated experimental strain and the standard strain, using the Yeast identification system, ID 32C (REF 32 200), bought from the bioMérieux® company.

A. The isolated experimental strain and the standard strain are cultured in 3 ml GYPY broth, 20° C., 150 rpm for 2 days.

B. Implement the experimental steps according to the kit operation manual.

C. The broths are cultured in 20° C. incubator for 3 days, and then the broths are taken from wells and added with ddH$_2$O to 1 ml to determine the concentration at O.D.$_{600}$. O.D. values less than 0.2 are viewed as no reaction (−), between 0.2-0.3 are viewed as the weak signal (W), between 0.4-0.6 are viewed as the strong signal (+), and more than 0.6 are viewed as the highest signal (++).

The results are shown in Table 2, and the classification of carbon sources are listed in Table 3. Comparing TN01 with the standard strain in utilizing carbon source, TN01 has the most similar utilizing carbon source to *C. bisporidii*, and the differences are lactic acid (LAT), methyl-D-glucopyranoside (MDG), palatinose (PLE) and sodium glucuronate (GRT) respectively.

TABLE 2

| | TN01 | C. bisporidii | C. capitatum | C. infirmominiatum |
|---|---|---|---|---|
| GAL | ++ | ++ | + | + |
| ACT | − | − | − | − |
| SAC | ++ | ++ | ++ | + |
| NAG | − | − | − | − |
| LAT | W | + | W | + |
| ARA | ++ | ++ | ++ | ++ |
| CEL | ++ | ++ | ++ | ++ |
| RAF | ++ | ++ | ++ | ++ |
| MAL | ++ | ++ | ++ | ++ |
| TER | ++ | ++ | ++ | ++ |
| 2KG | ++ | ++ | ++ | ++ |
| MDG | − | W | − | − |
| MAN | ++ | ++ | ++ | ++ |
| LAC | − | − | − | + |
| ION | ++ | ++ | ++ | ++ |
| 0 | − | − | − | − |
| SOR | ++ | ++ | ++ | ++ |
| XYL | ++ | ++ | + | ++ |
| RIB | ++ | ++ | − | ++ |
| GLY | ++ | ++ | ++ | ++ |
| RHA | ++ | ++ | − | ++ |
| PLE | W | + | − | ++ |

TABLE 2-continued

| | TN01 | C. bisporidii | C. capitatum | C. infirmominiatum |
|---|---|---|---|---|
| ERY | − | − | − | − |
| MEL | + | + | − | − |
| GRT | + | ++ | ++ | ++ |
| MLZ | ++ | ++ | ++ | ++ |
| GNT | ++ | ++ | + | ++ |
| LVT | − | − | − | − |
| GLU | ++ | ++ | ++ | ++ |
| SBE | ++ | ++ | ++ | − |
| GLN | − | − | − | − |
| ESC | − | − | − | − |

TABLE 3

| Test | Substrate |
|---|---|
| GAL | D-GALactose |
| ACT | cycloheximide (ACTidione) |
| SAC | D-SACcharose (sucrose) |
| NAG | N-Acetyl-Glucosamine |
| LAT | LacTic acid |
| ARA | L-ARAbinose |
| CEL | D-CELlobiose |
| RAF | D-RAFfinose |
| MAL | D-MALtose |
| TER | D-TREhalose |
| 2KG | potassium 2-KetoGluconate |
| MDG | Methyl-D-Glucopyranoside |
| MAN | D-MANnitol |
| LAC | D-LACtose (bovine origin) |
| ION | INOsitol |
| 0 | No substrate |
| SOR | D-SORbitol |
| XYL | D-XYLose |
| RIB | D-RIBose |
| GLY | GLYcerol |
| RHA | L-RHAmnose |
| PLE | PaLatinosE |
| ERY | ERYthritol |
| MEL | D-MELibiose |
| GRT | sodium GlucuRonaTe |
| MLZ | D-MeLeZitose |
| GNT | potassium GlucoNaTe |
| LVT | levulinic acid (LeVulinaTe) |
| GLU | D-GLUcose |
| SBE | L-SorBosE |
| GLN | GLucosamiNe |
| ESC | ESCulin ferric citrate |

Pick a colony on the solid medium to a tube containing 3 ml GYPG broth, placed in 20° C., 150 rpm for 2 days of shaking, and 500 μl broth are transferred into an 125 ml flask containing 50 ml GYPG broth, placed in 20° C., 150 rpm for 2 days of shaking to obtain final inoculum. 500 μl broth are taken from the final inoculum to each broth, every cultured condition repeats for 3 times, the cultured days are determined by the growth curve, broths containing TN01 are collected during the stationary phase, and the centrifugation and freeze drying are performed.

Fatty Acid Extraction

The freeze drying is performed for each collected cultured medium to obtain dried powder, and the fatty acid extraction is performed for the dried powder. Since fatty acid in organism exists in the form of triglyceride, which is the form of 3 free fatty acids combined with a glycerol via esterification, transesterification is needed. The transesterification is performed for Methanol and triglyceride to form single methyl esters to be analyzed.

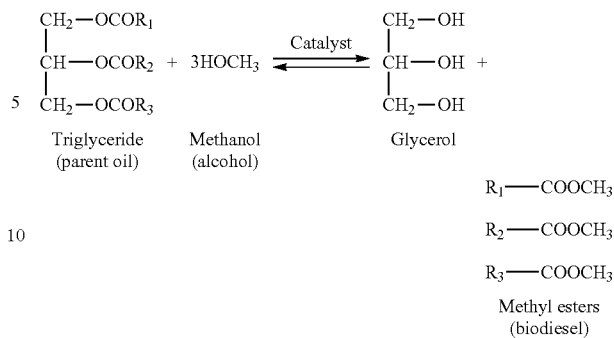

Transesterification of a Triglyceride (Chisti, 2007)

In the process of the extraction, Gas Chromatography (GC) is used to determine the quantity of fatty acid in the microorganisms, but the sample is really detected by a detector. Since the detector itself can not provide a stable detectable result due to the characteristic of GC, an internal standard is added to provide a quantifiable basis. The ratio of the analyte to the internal standard, named RRF (Relative Response Factor), is used to determine the quantity of the sample. Because the sample and the internal standard will present proportional increment and decrement in the detection process, more accurate quantification is available. For the choice of an internal standard, substances appearing in the sample and having a similar structure, chemical property and boiling point to the sample will not be chosen as an internal standard. Most fatty acids existing in organisms are even-carbon chains; odd-carbon chains are very rare. Thus, nonadecanoic acid is used as an internal standard. The extraction steps are as follows.

A. Take 0.05 g dried powder of fungus body into 10 ml tube, add 5 ml chloroform:methanol (2:1) and mix well.

B. The fungus body is shaken by ultrasonic waves for 2 min (shake 5 sec and stop 5 sec for totally 4 min)

C. After placed under room temperature for 1 hr, 100 μl 10 mg/ml internal standard is added.

D. Add 0.5 ml water, centrifugate at 2500 rpm for 5 min and then remove the suspension.

E. Add 2.5 ml TUP (theoretical upper phase, chloroform:ddH2O:methanol=47:48:3) without shaking, centrifugate at 2500 rpm for 5 min and then remove the suspension.

F. Repeat steps D and E, and dry the precipitate by nitrogen gas under room temperature.

G. Add 2.5 ml methanol-benzene 4:1 (V/V), slowly add 250 μl acetyl chloride as catalyst of transesterification, and mix well.

H. Cover the Teflon lid tightly and place in the 80° C. oven for 4 hr.

I. After cooled under room temperature, add 1.5 ml 7% $K_2CO_3$ slowly to stop the reaction, and centrifugate at 2500 rpm for 10 min.

J. Take the upper benzene layer to the discarded centrifugal tube, and dry the precipitate by nitrogen gas under room temperature.

K. Add 0.5 ml hexane along the tube wall and mix well.

L. After dried by nitrogen gas, add 250 μl hexane, mix well, and inject into the sample bottle having the insert tube. After sealing the opening, use GC to analyze.

Analyze Fatty Acid By Gas Chromatography (GC)

Figure 6:
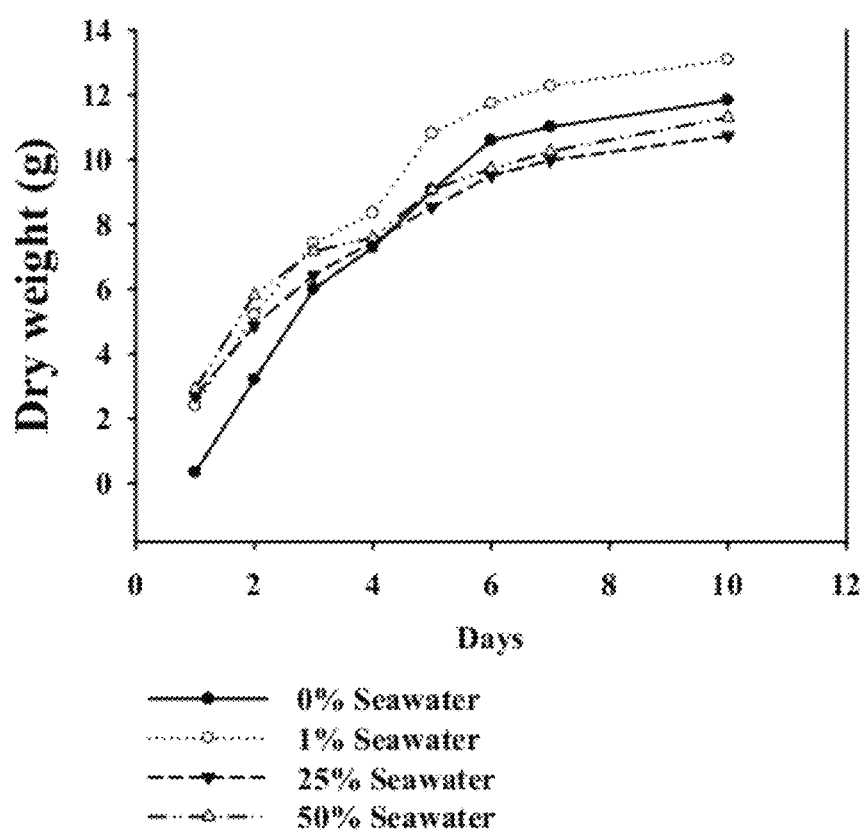
FIG. 6 shows the salt concentration test and the growth curve of TN01.

The adopted chromatographic column is lower polarity DB-1 having a length of 60 m and an inner diameter of 0.25 mm; the inner membrane of the chromatographic column is Dimethylpolysiloxane[—O—Si(CH$_3$)$_2$—], and the thickness thereof is 0.25 μm; the initial temperature of the oven is 60° C. and heat to 280° C.; the heating temperature of the injector is 250° C.; the flow rate of nitrogen gas is 1.2 ml/min, the flow rate of hydrogen gas is 30 ml/min, and the flow rate of air is 300 ml/min; the injection amount of the sample is 1 μl; the fire ion detector (FID) is used for detecting sample; and the temperature is set to 300° C. The result is integrated by GC kit software, and fatty acid contents are estimated by the standard. The estimated equation is:

Single fatty acid %=(integration area of single fatty acid*concentration of the standard*100)/integration area of the internal standard Total fatty acid %=[(integration area of total fatty acid–integration area of the internal standard)*concentration of the standard*100]/integration area of the internal standard Optimal Salt Concentration Test The medium is added with diluted seawater by 0%, 1%, 25% and 50% respectively, and 5 L fermentation tank culture is performed. 50 ml cultural medium is collected every 24 hr to be freeze dried, and then the dry weight thereof is measured to estimate the collected total fungus bodies and cultural days. FIG. 6 shows the growth standard curve of TN01 under each test of salt concentration conditions. The 1$^{st}$-5$^{th}$ days are the log phase of TN01, the growth rate of TN01 starts to become mild on the 6$^{th}$ day, and the growth rate becomes slow during the 7$^{th}$-10$^{th}$ days, but still shows an upward tendency, so the 6$^{th}$ day is determined to collect fungus bodies for the subsequent optimal culture. The best salt concentration of growth is 1% seawater, the worst is 25%, and 0%, 50% are the second best. After culturing for 10 days, the dried weight of fungus body under 1% seawater condition has reached 13.09 g/L, and 0%, 25% and 50% correspond to 11.84 g/L, 10.73 g/L and 11.31 g/L respectively.

Figure 7:
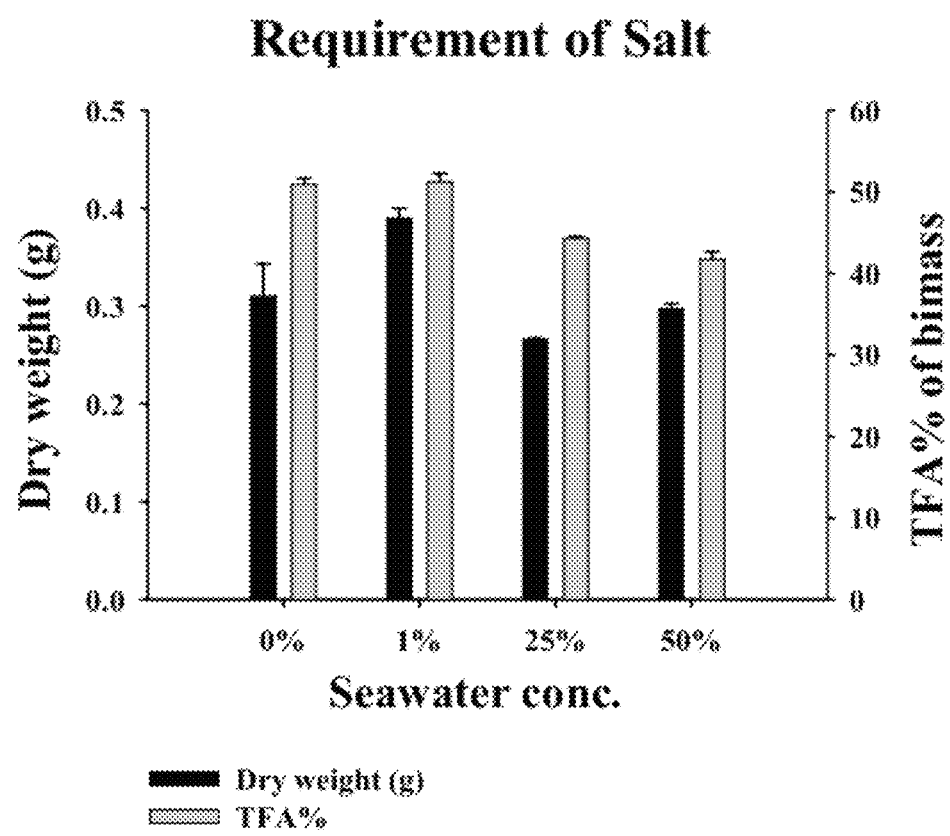
FIG. 7 shows the optimal cultural salt concentration test of TN01.

The fungus body of the growth of the 6$^{th}$ day is collected to determine the dried weight and analyze the fatty acid contents, which are shown in FIG. 7. The dried weight of fungus body (50 ml) of 0%, 1%, 25% and 50% of seawater concentration are 0.31 g, 0.39 g, 0.266 g and 0.297 g respectively; total fatty acid contents are 50.91%, 51.24%, 44.31% and 41.76% respectively. Comparing the results of growth curve with the fatty acid analysis, the subsequent optimal experiments all adopt 1% seawater.

Range Test of Cultural Temperature

Figure 8:
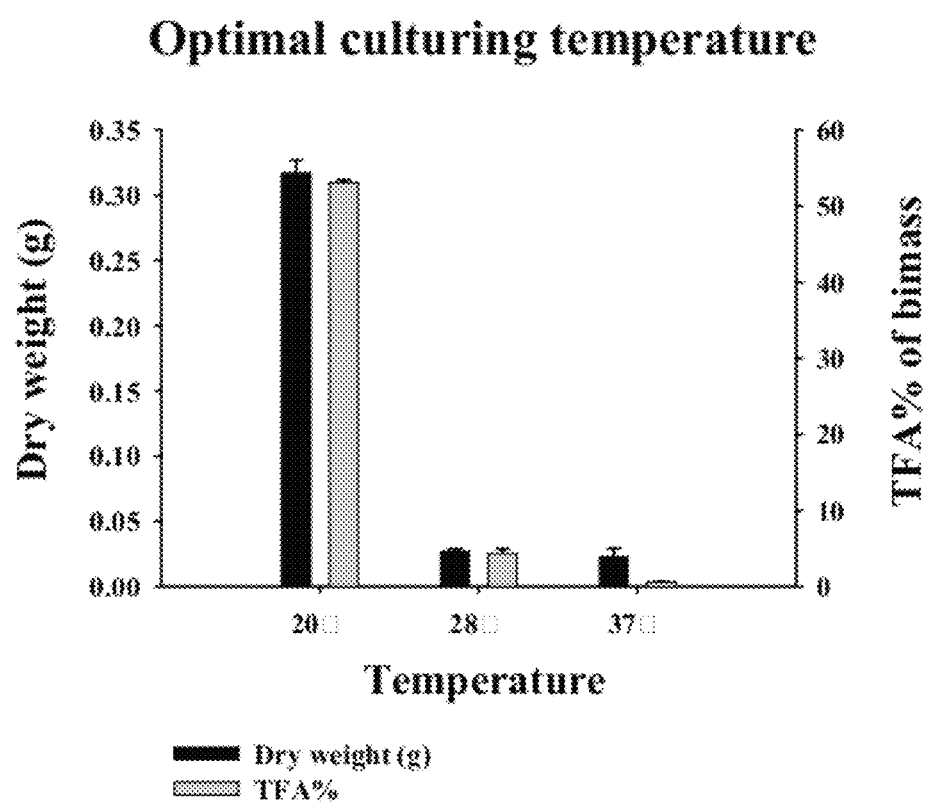
FIG. 8 shows the optimal cultural temperature test of TN01.

TN01 is cultured in 50 ml GYPG broth under 3 different temperatures, and fungus bodies are collected after culturing for 6 days. The analysis results of dried weight and fatty acid are shown in FIG. 8. There are the best biomass and percentage of fatty acid cultured in 20° C., bad in 28° C., and TN01 almost can not grow in 37° C., which is quite different from 20° C.

The dried weights of fungus body cultured in 20° C., 28° C. and 37° C. are 0.317 g, 0.027 g and 0.023 g respectively, and total fatty acid contents are 53.1%, 4.40% and 0.63% respectively.

Cultured Medium Simplification

When the fermentation and culture are to be performed in industrial scale in the future, the simplest medium is desired to be used to lower the cost. Therefore the original GYPG medium is improved as follows:

|      | Glucose | Yeast Extract | Peptone | Gelatin |
|------|---------|---------------|---------|---------|
| GYPG | 5%      | 0.1%          | 0.1%    | 0.1%    |
| GYP  | 5%      | 0.1%          | 0.1%    | —       |
| GYG  | 5%      | 0.1%          | —       | 0.1%    |
| GY   | 5%      | 0.1%          | —       | —       |

Figure 9:
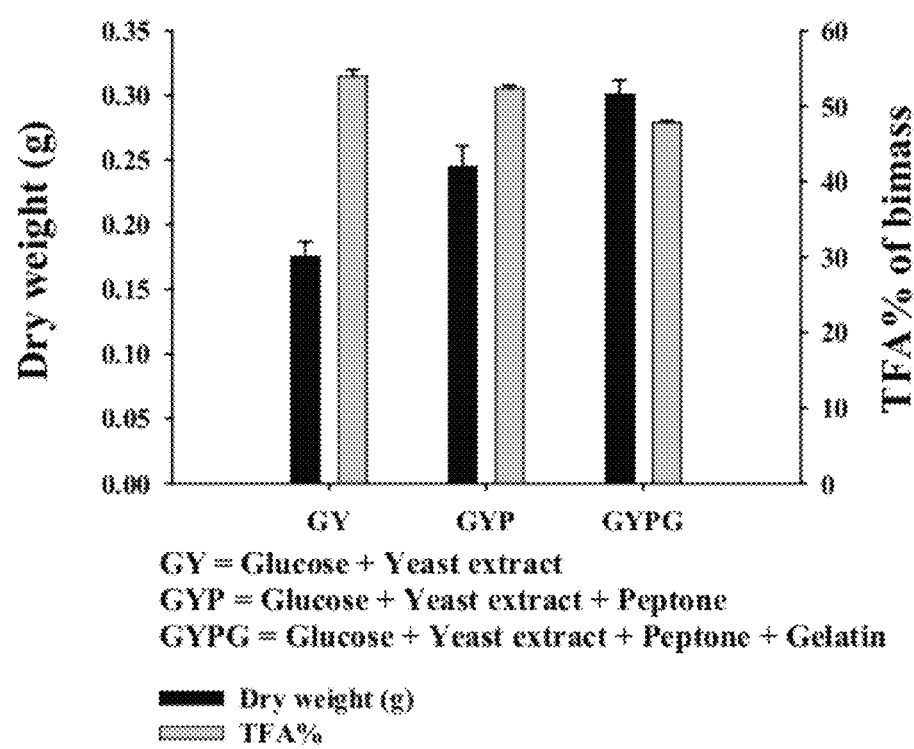
FIG. 9 shows the medium simplification test of TN01.

Different simplified mediums are used to test the growth condition and the fatty acid accumulation of TN01. TN01 is cultured in 50 ml experimental broth, and after cultured for 6 days, broths containing TN01 are collected and dried to determine the dried weight and analyze the total fatty acid contents whose results are shown in FIG. 9. The dried weight of TN01 cultured in GY, GYP and GYPG are 0.1750 g, 0.2450 g and 0.3010 g respectively, and the total fatty acid contents are 53.96%, 52.35% and 47.84% respectively. TN01 cultured in GYPG has the highest dried weight, but the lowest fatty acid content; TN01 cultured in GY has a reverse result. Considering the large difference in dried weight, the subsequent experiments still use GYPG.

Optimal pH Value Test

The range of pH values is set as 3-11 to discuss the effect of pH values on the fungus body and the optimal cultural condition. To take out the effect of metabolites generated by the organisms on pH values, based on the GYPG broth, the following buffers are added according to each condition.

| pH value | Buffer and concentration thereof |
|----------|----------------------------------|
| 3-4      | Sodium Acetate, 30 mM            |
| 5-6      | MES, 30 mM                       |
| 7-8      | Tris, 30 mM                      |
| 9-11     | CAPSO, 30 mM                     |

The pH value is adjusted by using acetic acid for pH 3-4 and using NaOH or HCl for pH 5-11.

Figure 10:
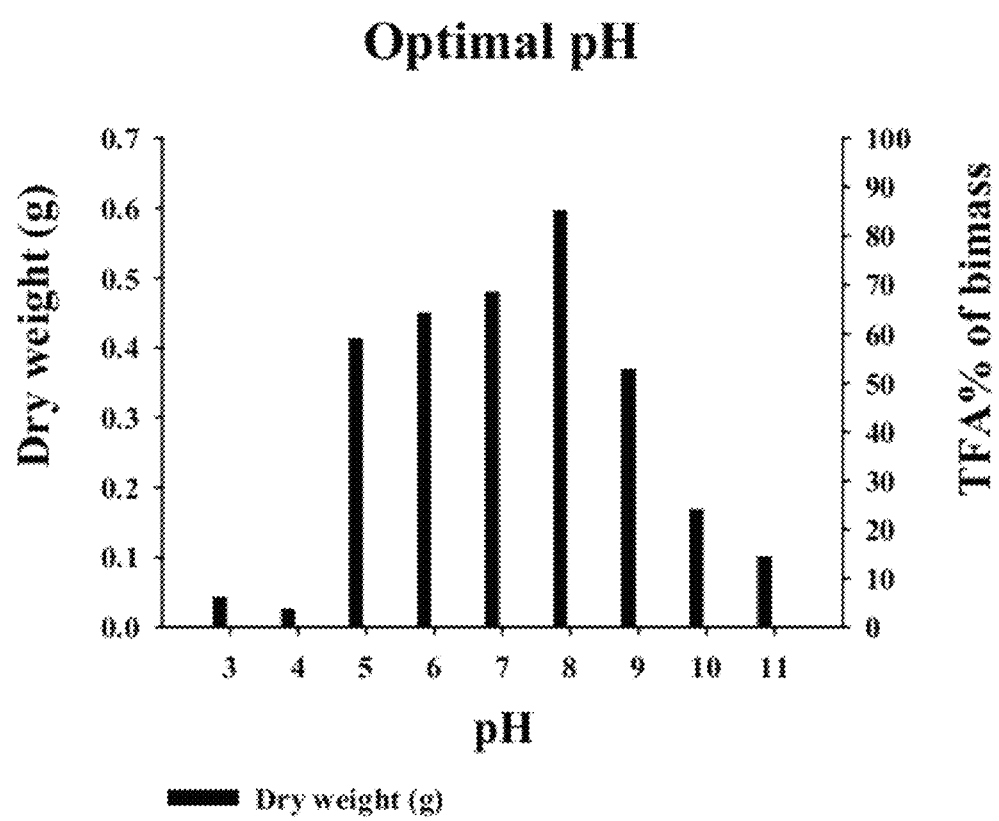
FIG. 10 shows the optimal cultural pH value test of TN01.

TN01 is cultured under each pH value, the optimal temperature and 150 rpm for 6 days. After 6 days, 50 ml broth is collected and dried to determine the dried weight whose results are shown in FIG. 10. For pH value 3-11, the dried weights are 0.0423 g, 0.025 g, 0.412 g, 0.45 g, 0.479 g, 0.596 g, 0.369 g, 0.168 g and 0.1 g respectively, and thus the optimal pH value for growth is pH 8.

Test of Utilizing the Carbon Source

The heterotroph needs the carbon source to grow. The utilization of type of carbon source affects the growth of microorganism and the accumulation of oil. According to the metabolic pathway of Saccharomyces, various carbon sources including monosaccharide (hexose and pentose), disaccharide, polysaccharide are used, and glycerol is used as the carbon source for oil so as to find the best carbon source for the growth of microorganism and the accumulation of oil. The cultural prescription is as follows.

5% carbon source+0.1% Yeast extract+0.1% Peptone+0.1% Gelatin

Figure 11:
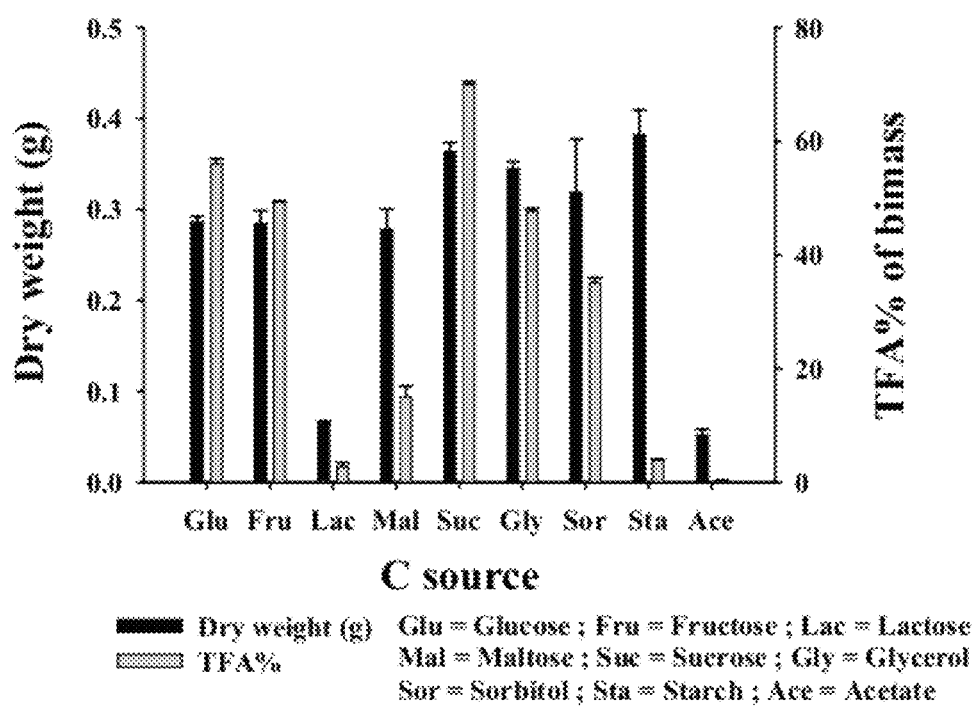
FIG. 11 shows the optimal cultural carbon source test of TN01.

Type of the carbon source: glucose, fructose, lactose, maltose, sucrose, glycerol, sorbitol, starch, acetate The results of the dried weight and the total fatty acid content are shown in FIG. 11. The carbon source for the best biomass of TN01 is starch whose dried weight is 0.382 g, and the second best is sucrose whose dried weight is 0.364 g; the carbon source for the best total fatty acid content of TN01 is sucrose whose content is 70%, and the second best is glucose whose content is 56%. TN01 cultured in lactose and acetate has the worst biomass and the lowest fatty acid content.

Test of Utilizing the Nitrogen Source

The nitrogen source is necessary nutrition for the growth of microorganisms. There are researches pointing out that different nitrogen sources affect oil accumulation of microorganisms. Therefore in this case, the organic nitrogen source and the inorganic nitrogen source are designed for observing the condition of the growth of microorganisms and the accumulation of oil so as to find the best nitrogen source. The cultural prescription is as follows.

5% Glucose+0.1% Yeast extract+0.1% Nitrogen source+ 0.1% Gelatin

Type of the nitrogen source: peptone, tryptone, soytone, ammonium nitrate, ammonium sulfate, ammonium chloride, sodium ammonium sulfate, sodium thiosulphate.

Sodium thiosulphate does not have the nitrogen source, and serves as a control.

Figure 12:
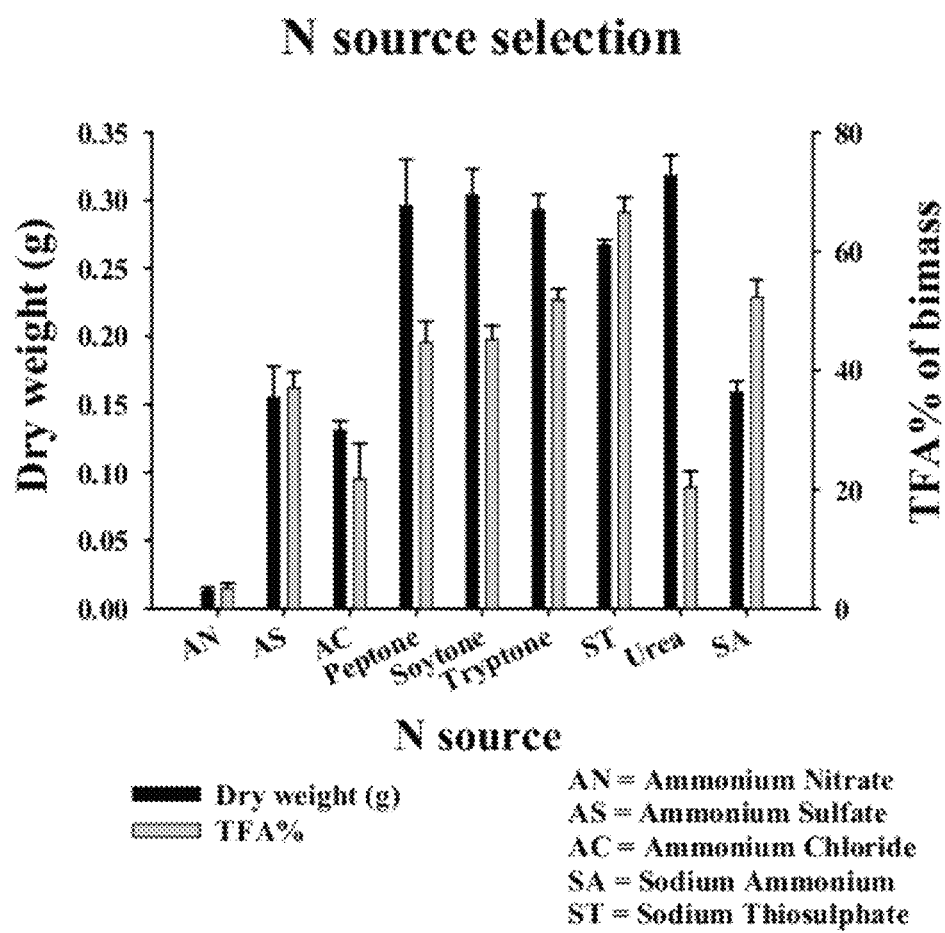
FIG. 12 shows the optimal cultural nitrogen source test of TN01.

The results of the dried weight and the total fatty acid content are shown in FIG. 12. The nitrogen source for the best biomass of TN01 is urea whose dried weight is 0.318 g, and the second-fourth best are soytone, peptone and tryptone whose dried weights are 0.304 g, 0.296 g and 0.293 g respectively; the nitrogen source for the best total fatty acid content of TN01 is the control, sodium thiosulphate (ST), whose content is 66.6%, and the second-third best are sodium ammonium sulfate (SA) and tryptone whose content contents are 52.3% and 51.9% respectively.

Test of High Sugar Concentration

Carbon is a basic unit of forming fatty acid, and fermentation culture usually uses fed-batch to adjust accumulation of the oil. Therefore, the test of high sugar concentration is designed to observe the effects of the growth of microorganisms and if fatty acid is increased under the condition of high-concentration sugar as a carbon source. Experimental sets use GYPG broth as the base, and the addition of glucose are 50 g/L, 100 g/L, 150 g/L and 200 g/L respectively.

Figure 13:
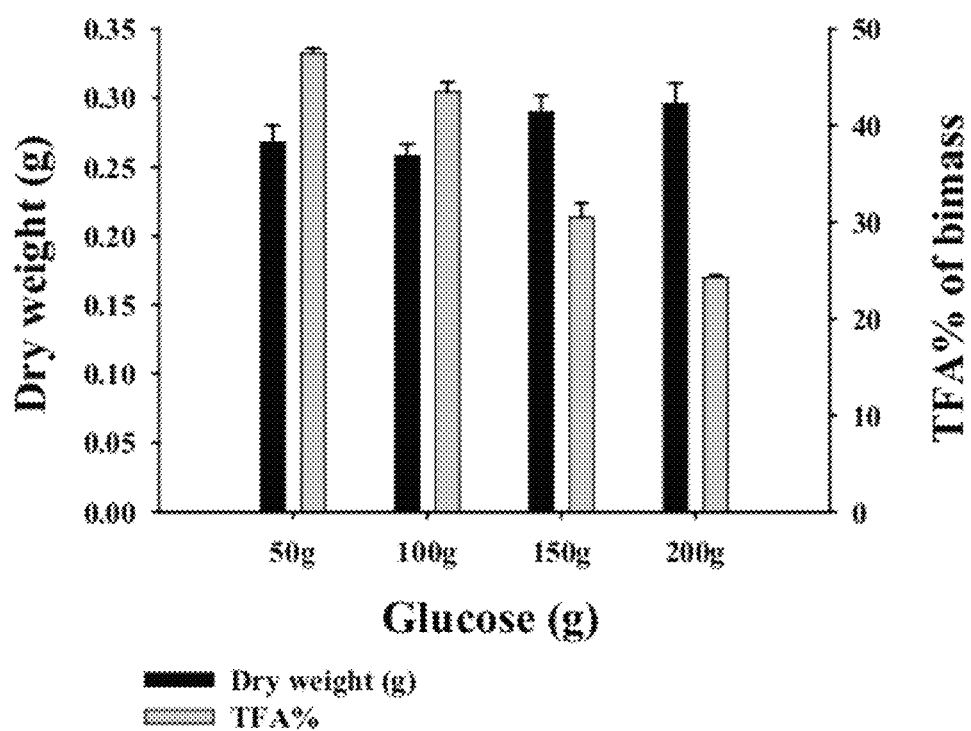
FIG. 13 shows the high sugar concentration test of TN01.

The results are shown in FIG. 13. Glucose concentration of 50 g/L, 100 g/L, 150 g/L and 200 g/L result in the dried weight of the fungus body being 0.2680 g, 0.2580 g, 0.2900 g and 0.2960 g respectively, and fatty acid content being 47.5%, 43.5%, 30.5% and 24.3% respectively. There are the best biomass under the glucose concentration of 150 g/L and the best fatty acid content under the glucose concentration of 50 g/L.

Classification of Fatty Acid of TN01

TN01 is cultured in GYPG broth, and after dried, fungus bodies are collected and fatty acid is extracted therefrom. In order to know the detailed classification of fatty acid of TN01, the GC-MS analysis is performed for the extracted sample. Most of fatty acids of TN01 are lower saturated fatty acids, as shown in Table 4, which are C14, C16 and C18 series. The lower saturated fatty acids are less easily oxidized, and are more suitable for the manufacture of biodiesel oil. Heat and oxidizing agent in the manufacture of biodiesel oil may split the saturated fatty acid, and there is an extra cost burden of adding anti-oxidizing agent. Additionally, TN01 has up to 50% total fatty acid before the optimal treatment, so it has high potential for serving as a source of biodiesel oil.

TABLE 4

| Type of fatty acid | Content of occupying the total fatty acid (%) |
|---|---|
| C14:0 | 17.34 |
| C16:0 | 20.4 |
| C18:0 | 4.69 |
| C18:1 | 40.47 |

TABLE 4-continued

| Type of fatty acid | Content of occupying the total fatty acid (%) |
|---|---|
| C18:2 | 11.47 |
| C18:3 | 2.41 |
| C20:4 | 0.97 |
| TFA % | 50.91 |

Test of the Fatty Acid Contents of TN01 and Other *Cystofilobasidium*

TN01, *Cystofilobasidium bisporidii* BCRC 22462, *Cystofilobasidium capitatum* BCRC 22464 and *Cystofilobasidium infirmominiatum* BCRC 22465 (BCRC: Bioresource Collection and Research Center) are cultured in the following medium.

| | |
|---|---|
| Glucose | 5% |
| Peptone | 0.1% |
| Yeast extract | 0.1% |
| Gelatin | 0.1% |
| Diluted seawater | 1% |
| Streptomycin | 0.1 g/L |

The brothes are placed at 20° C., 150 rpm for 7 days of shaking. The results of fatty acid content are shown in Table 5. Other *Cystofilobasidium* indeed have the ability of generating oil, but are not better than TN01.

TABLE 5

| | GC peak Area percentage (%) Strain | | | |
|---|---|---|---|---|
| FA | TN 01 | 22462 | 22464 | 22465 |
| C14:0 | 17.343 | | | |
| C16:0 | 20.396 | 19.69 | 17.35 | 13.97 |
| C16:1 | | 1.14 | | |
| C18:0 | 4.692 | 3.86 | 3.18 | 1.26 |
| C18:1 | 40.474 | 10.53 | 8.85 | 23.61 |
| C18:2 | 11.47 | 23.7 | 27.08 | 11.53 |
| C18:3 | 2.407 | | | |
| C20:0 | | | 1.14 | |
| C24:0 | 0.971 | 1.65 | | |
| TFA/Biomass (%) | 50.91 | 33.56 | 33.22 | 17.29 |

*Cystofilobasidium* spp. TN01 was deposited in China General Microbiological Culture Collection Center on Jun. 20, 2011, under the rules of Budapest Treaty, and the deposit number was CGMCC No. 4968.

Embodiments

1. An oil generation system, including:
a saccharide; and
a working microorganism reacting with the saccharide to produce an oil, wherein the working microorganism has a genus being a *Cystofilobasidium*.

2. An oil generation system of Embodiment 1, further including a nitrogen source utilized by the working microorganism, wherein the nitrogen source includes a sodium ammonium sulfate.

3. An oil generation system of any one of Embodiments 1-2, wherein the saccharide includes a sucrose.

4. An oil generation system of any one of Embodiments 1-3, wherein the oil includes a fatty acid of C14-C20.

5. An oil generation system of any one of Embodiments 1-4, wherein the oil includes an unsaturated fatty acid.

6. An oil generation system of any one of Embodiments 1-5, wherein the working microorganism has a 18S rDNA sequence of SEQ ID NO:7.

7. An oil generation system of any one of Embodiments 1-6, wherein the working microorganism has a 26S rDNA sequence of SEQ ID NO:8.

8. An oil generation system of any one of Embodiments 1-7, wherein the working microorganism has an ITS sequence of SEQ ID NO.9.

9. An oil generation system, including:
a carbon source; and
a working microorganism reacting with the carbon source to produce an oil, wherein the working microorganism has a genus being a *Cystofilobasidium*.

10. An oil generation system of Embodiment 9, wherein the working microorganism breaks down the carbon source to produce the oil.

11. An oil generation system of any one of Embodiments 9-10, wherein the carbon source includes a saccharide.

12. A method for producing an oil, including a step of utilizing an oil-generating microorganism to produce the oil, wherein the oil-generating microorganism has a genus being a *Cystofilobasidium*.

13. A method of Embodiment 12, wherein the oil-generating microorganism includes one selected from a group consisting of a *Cystofilobasidium bisporidii*, a *Cystofilobasidium capitatum*, a *Cystofilobasidium infirmominiatum* and a combination thereof.

14. A method of any one of Embodiments 12-13, wherein the step of utilizing the oil-generating microorganism to produce the oil includes a step of breaking a carbon source by the oil-generating microorganism.

15. A method of any one of Embodiments 12-14, wherein the carbon source includes a sucrose.

16. A method of any one of Embodiments 12-15, further including a step of providing a nitrogen source to be utilized by the oil-generating microorganism, wherein the nitrogen source includes a sodium ammonium sulfate.

17. A method of any one of Embodiments 12-16, wherein the oil-generating microorganism has a 18S rDNA sequence of SEQ ID NO.7.

18. A method of any one of Embodiments 12-17, wherein the oil-generating microorganism has a 26S rDNA sequence of SEQ ID NO.8.

19. A method of any one of Embodiments 12-18, wherein the oil-generating microorganism has an ITS sequence of SEQ ID NO.9.

20. A method of any one of Embodiments 12-19, further including a step of using the oil as a biodiesel oil.

Based on the above, the present invention effectively solves the problems and drawbacks in the prior art, and thus it fits the demand of the industry and is industrially valuable.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An oil generation system, comprising:
   a saccharide; and
   an isolated working microorganism reacting with the saccharide to produce an oil, wherein the isolated working microorganism has a genus being a *Cystofilobasidium* comprising a 18S rDNA sequence of SEQ ID NO.7, wherein the oil includes a fatty acid of C14-C20.

2. The system as claimed in claim 1, further comprising a nitrogen source utilized by the isolated working microorganism, wherein the nitrogen source includes a sodium ammonium sulfate.

3. The system as claimed in claim 1, wherein the saccharide includes a sucrose.

4. The system as claimed in claim 1, wherein the oil includes an unsaturated fatty acid.

5. The system as claimed in claim 1, wherein the isolated working microorganism has a 26S rDNA sequence of SEQ ID NO.8.

6. The system as claimed in claim 1, wherein the isolated working microorganism has an internal transcribed spacer (ITS1 sequence of SEQ ID NO.9.

7. An oil generation system, comprising:
   a carbon source; and
   an isolated working microorganism reacting with the carbon source to produce an oil, wherein the isolated working microorganism has a genus being a *Cystofilobasidium* comprising a 26S rDNA sequence of SEQ ID NO.8.

8. The system as claimed in claim 7, wherein the isolated working microorganism breaks down the carbon source to produce the oil.

9. The system as claimed in claim 7, wherein the carbon source includes a saccharide.

10. A method for producing an oil, comprising a step of utilizing the oil generation system as claimed in claim 1 comprising an isolated working microorganism to produce the oil.

11. A method as claimed in claim 10, wherein the isolated working microorganism includes one selected from a group consisting of a *Cystofilobasidium bisporidii*, a *Cystofilobasidium capitatum*, a *Cystofilobasidium infirmominiatum* and a combination thereof.

12. A method as claimed in claim 10, wherein the step of utilizing the oil generation system as claimed in claim 1 to produce the oil comprises a step of breaking a carbon source by the isolated working microorganism.

13. A method as claimed in claim 12, wherein the carbon source includes a sucrose.

14. A method as claimed in claim 10, further comprising a step of providing a nitrogen source to be utilized by the isolated working microorganism, wherein the nitrogen source includes a sodium ammonium sulfate.

15. A method as claimed in claim 10, wherein the isolated working microorganism has a 26S rDNA sequence of SEQ ID NO.8.

16. A method as claimed in claim 10, wherein the isolated working microorganism has an ITS sequence of SEQ ID NO.9.

17. A method as claimed in claim 10, further comprising a step of using the oil as a biodiesel oil.

* * * * *

UNITED STATES PATENT AND TRADEMARK OFFICE
CERTIFICATE OF CORRECTION

PATENT NO. : 8,685,699 B2  Page 1 of 1
APPLICATION NO. : 13/204116
DATED : April 1, 2014
INVENTOR(S) : Leu et al.

It is certified that error appears in the above-identified patent and that said Letters Patent is hereby corrected as shown below:

IN THE CLAIMS:
In claim 6, column 19, line 48, change "(ITS1 sequence of SEQ ID NO.9." to --(ITS) sequence of SEQ ID NO. 9.--

Signed and Sealed this
Second Day of September, 2014

Michelle K. Lee
*Deputy Director of the United States Patent and Trademark Office*